United States Patent [19]

Gilles et al.

[11] Patent Number: 4,635,646
[45] Date of Patent: Jan. 13, 1987

[54] PORTABLE APPARATUS FOR MONITORING HEART ACTIVITY

[76] Inventors: Ascher Gilles, 20bis bd du Général Leclerc, 92200 Neuilly; Jean-Pierre Coustenoble, 11 rue Charcot, 92800 Puteaux; Jean-François Fournial, La Sauvagère Route de Parinier, 72560 Change, all of France

[21] Appl. No.: 662,024

[22] Filed: Oct. 18, 1984

[30] Foreign Application Priority Data

Nov. 10, 1983 [FR] France ................................ 83 17874

[51] Int. Cl.⁴ ................................................ A61B 5/04
[52] U.S. Cl. ..................................... 128/696; 128/706
[58] Field of Search .................... 128/689–690, 128/696, 701–704, 706, 708, 711, 904, 644

[56] References Cited

U.S. PATENT DOCUMENTS

| | | | |
|---|---|---|---|
| 2,848,992 | 8/1958 | Pigeon | 128/706 |
| 3,144,018 | 8/1964 | Head | 128/701 |
| 3,464,404 | 9/1969 | Mason | 128/640 |
| 3,534,727 | 10/1970 | Roman | 128/644 |
| 3,565,058 | 2/1971 | Mansfield | 128/701 |
| 4,193,393 | 3/1980 | Schlager | 128/706 |
| 4,230,127 | 10/1980 | Larson | 128/644 |
| 4,295,472 | 10/1981 | Adams | 128/690 |
| 4,457,315 | 7/1984 | Bennish | 128/711 |

Primary Examiner—William E. Kamm
Attorney, Agent, or Firm—Bachman & LaPointe

[57] ABSTRACT

A portable apparatus for monitoring heart activity, including two electrodes connected to a case which encloses an electronic signal processor. The electrodes are separate and applied to different parts of the cardiac region of the patient's bust, one electrode being exposed on a face of the case to contact a first zone on the patient's bust, the other electrode being independent of the case and contacting a second zone of the bust, the electrodes being connected electrically by a conductor which also serves as a strap to suspend the apparatus on the patient's body.

13 Claims, 8 Drawing Figures

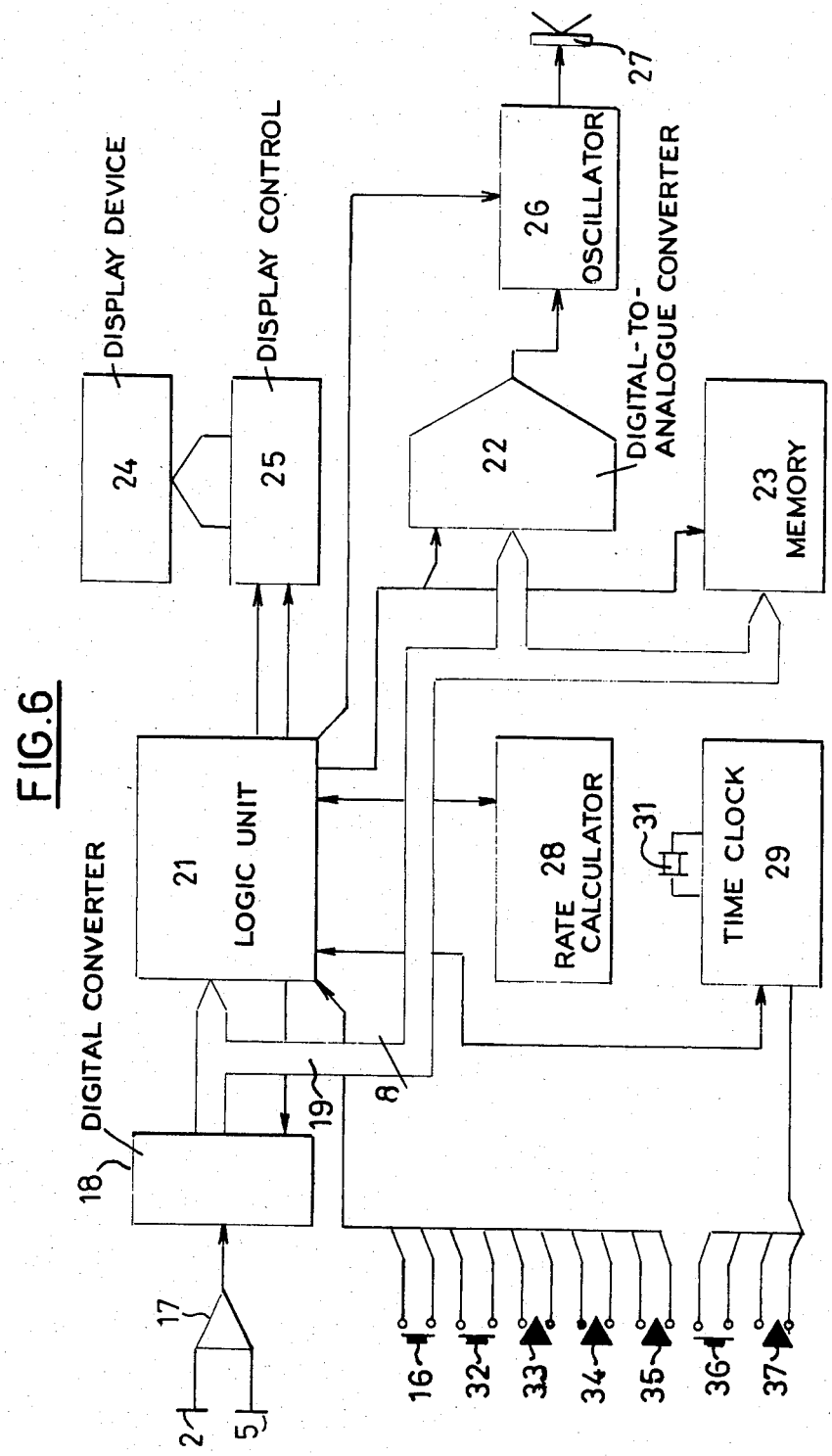

PORTABLE APPARATUS FOR MONITORING HEART ACTIVITY

BACKGROUND OF THE INVENTION

The present invention relates to portable apparatus for monitoring heart activity in varied circumstances without a medical specialist being present.

DESCRIPTION OF THE PRIOR ART

Apparatus has been proposed comprising a case presenting two electrodes for picking up electrocardiograms; the case containing an electronic processor device which records the electrocardiograms for subsequent transmission to the doctor treating the patient or which registers the value of the pulse rate of the person.

Apparatus of this kind comprises a case of the shape and size of a packet of cigarettes and bearing two external electrodes to which the patient's hands are applied to register an electrocardiogram at the very moment when a malaise occurs, and this is very important for patients whose symptoms recur with low frequency. The electrocardiogram thus recorded is digitalised and stored in a memory so that it can be read out subsequently by a specialist doctor.

Although such apparatus is portable, it is not immediately accessible, since it generally has to be taken out of a pocket, the electrodes have to be found and contacted by the patient's hands; although these operations are simple they take a time which is appreciable in the bother which surrounds the occurrence of a malaise and the electrocardiogram recorded may not be characteristic since it may be too late in the evolution of the malaise. Also, such an apparatus is not always available, for example if it is left in a garment that the patient has taken off, or if the patient's clothes do not have a pocket, which is especially the case with some summer and sports clothing.

Moreover, since the recording is taken between the patient's hands, parasites or artefacts occur and cannot be eliminated, which reduces the quality of the recording of the electrocardiogram.

OBJECT OF THE INVENTION

An object of the present invention is to reduce or eliminate some or all of the above disadvantages.

BRIEF DESCRIPTION OF THE INVENTION

The present invention provides a portable apparatus for monitoring heart activity comprising a case, a first electrode mounted on said case, a second electrode separate from said case, attachement means for attaching said apparatus to a patient's body, with said first and second electrodes applied in electrical contact with respective regions of the patient's bust whereby said electrodes pick up diastolic and systolic electrocardiogram signals, said attachment means including a flexible loop for passing round a part of the patient's bust, said loop including electrical conductor means for connecting said second electrode means electrically with said case, and said case including electronic processing means for registering said electrocardiogram signals.

At least one of the electrodes is in permanent contact with the patient's bust, and the other electrode can rapidly be brought into contact (if it is not in permanent contact) with another part of the patient's bust so as to pick up signals from the diastolic and systolic activity of the patient's heart. This operation is particularly rapid since it can be arranged so that it is sufficient for the patient to press the case against his chest to trigger the recording.

Moreover, the electrodes being in contact with the patient's bust, in the cardiac region, the signals obtained are relatively free from parasites and are of a quality comparable to signals obtained by fixed electrocardiograms recording apparatus such as normally used in hospitals and doctor's surgeries.

In an embodiment of the invention, the flexible loop is passed round the patient's neck, like a necklace. The first and second electrodes are at substantially opposite sides of the loop so that the case hangs like a prendant from the loop on the patient's chest, while the second electrode is applied against the nape of the patient's neck.

The second electrode is then in permanent contact with the nape of the patient's neck, and the first electrode can rapidly be applied to the patient's chest to make a recording when a malaise occurs. It should be noted that the gesture of bringing the hand up to the chest is a natural gesture when a heart malaise causes a pain, and consequently the gesture can be arranged to trigger a recording of an electrocardiogram almost instinctively. The second electrode is maintained in permanent contact with the patient's skin by the loop and the weight of the case hanging on the loop.

The use of a flexible loop enables the apparatus to fit different morphologies of different patients. The patient can immediately apply the case to a suitable part of his chest, regardless of his individual morphology.

According to a preferred feature of the invention, said first and second electrodes are flexible and comprise interwoven conductors.

According to another preferred feature of the invention, at least one auxiliary electrode, fixing means for fixing said auxiliary electrode to the patient's skin, and electrical connection means for connecting said auxiliary electrode with said case.

Preferably, said electrical connection means includes mechanical and electrical couplings for coupling said first electrode to said auxiliary electrode. In a preferred embodiment, said electronic processing means includes analogue-to-digital convertor means responsive to signals from said electrodes, digital storage means for storing signals from said analogue-to-digital convertor means, and manually actuable trigger means for triggering storage of said signals in said storage means. Advantageously, said storage means includes rotating storage means continually responsive to said signals, and said trigger means is effective to cause permanent storage of the signals in said rotating storage means, whereby to record an electrocardiogram corresponding to a period previous to manual actuation of said trigger means. This arrangement enables the apparatus to function continually in permanent monitoring or "sentinel" mode, the electrocardiogram being recorded as desired, and including a record of the situation prior to the moment when the recording was triggered.

In yet another preferred feature of the invention, said electrical connection means including an auxiliary case of generally thin and flat shape presenting two faces on which are disposed male and female coupling members respectively, whereby said auxiliary case may be connected electrically and mechanically with said electrical connection means between said case and said auxiliary electrode, further auxiliary electrodes fixing means for fixing said further auxiliary electrodes to different regions of the patient's bust, and flexible electrical connector means for connecting said further auxiliary electrodes with said auxiliary case. With this arrangement, different types of recording may be made from different paris of electrodes, and the recording obtained is almost identical to that obtained from a fixed electrocardiogram recording installation.

DESCRIPTION OF THE DRAWINGS

Other features and advantages of the invention will appear from the following description, given by way of example, with reference to the accompanying drawings, in which:

FIG. 6 is a schematic diagram of an example of an electronic signal processing device in the apparatus;

DESCRIPTION OF PREFERRED EMBODIMENTS OF THE INVENTION

Figures 1, 2:
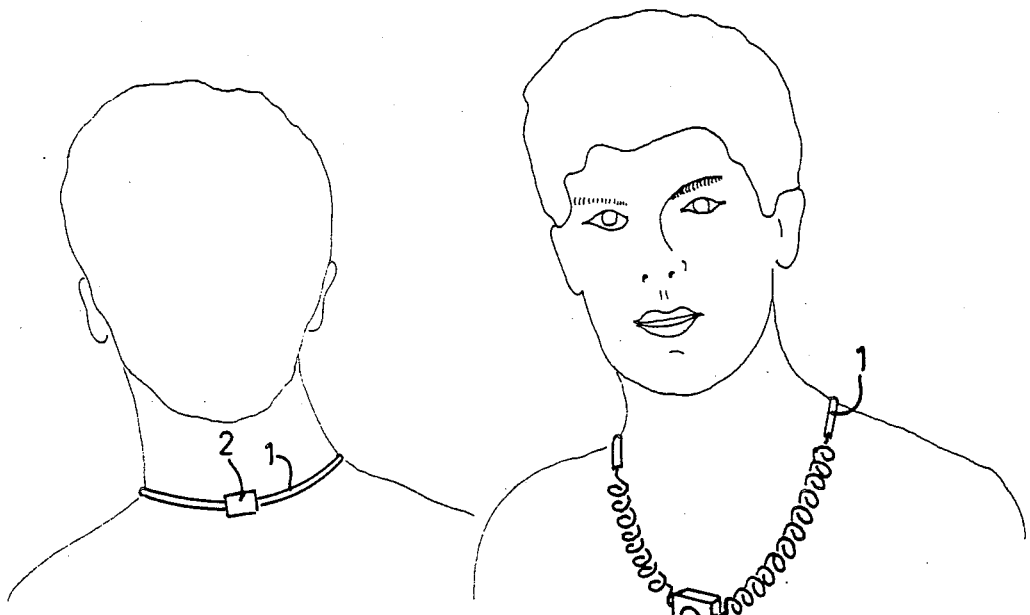
FIGS. 1 and 2 are rear and front views, respectively of a patient wearing an apparatus in accordance with an embodiment of the invention.

The apparatus shown in the drawings is a portable cardiac activity monitor including two separate electrodes, one of which is mounted on a case enclosing an electronic signal processing device and the other of which is connected with the case by a conductive link which also serves to suspend and/or maintain the case on the patient's body. The electrical link can take different forms, such as a harness, or shoulder strap worn on the patient's bust. In the embodiment shown in FIGS. 1 and 2, the electrical link or conductor 1 comprises a flexible strap in the form of a loop which is passed round the patient's neck and which carries a remote electrode 2 which is applied to the nape of the patient's neck, the strap 1 also carrying the case 3 which encloses the electronic signal processing device, the case 3 bearing another electrode on its rear face. The strap 1 may be formed in a spiral, as shown in FIG. 2, so as to be sufficiently elastic to enable the case 3 to be moved into contact with different zones of the patient's chest.

The remote electrode 2 comprises a small thin case bearing a flat electrode on one face, in contact with the patient's skin; similarly, one face of the case 3 bears an electrode 5 which contacts the patient's bust. These two electrodes are preferably made of a mail or braid type of conductive material, which enables the electrode to be flexible and to deform to fit the profile of the part of the patient's bust to which it is applied. This embodiment of the electrode therefore enables good contact to be obtained even in the case where the zone to which the electrode is applied is very hairy.

In accordance with this embodiment of the invention, at least one of the electrodes comprises a mechanical coupling and electrical connector for connecting it with an auxiliary electrode which is permanently adhered to the patient's bust, the auxiliary electrode comprising a complementary coupling.

Figure 3:
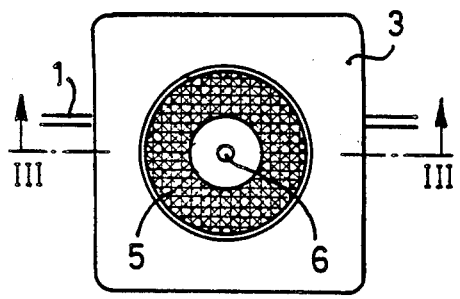
FIG. 3 is an elevational view of the rear face of a case in the apparatus of FIGS. 1 and 2, with an electrode on it.
Figure 4:
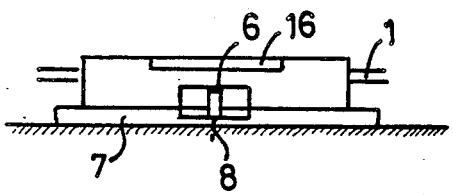
FIG. 4 is a sectional veiw of the case on the line III—III of FIG. 3, with an auxiliary electrode.

In the embodiment shown, the mechanical coupling comprises a clip device of the press-stud kind, the main electrode comprising the female part of the coupling and the auxiliary electrode comprising the male part. This coupling is shown particularly in FIGS. 3 and 4 where the female part 6 of the press-stud is formed in the face of the case 3, so that the face is free from projections, and the auxiliary electrode 7 is provided with the male part 8 for cooperating with the female part 6. Preferably, in this case, the auxiliary electrode 7 has adhesive on both sides so that the case 3 adheres well to the skin and does not tend to pull the electrode down. The auxiliary electrode 7 can also be provided with a similar press-stud type mechanical coupling. The auxiliary electrodes may be ambulatory electrodes, known as Holter electrodes.

Figure 5:
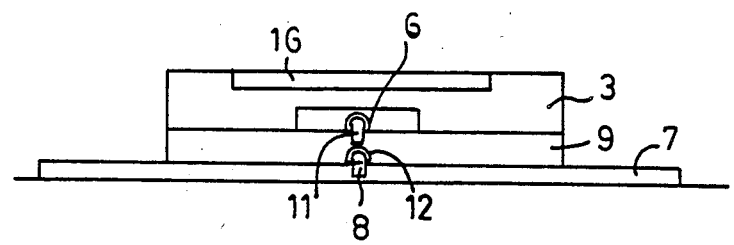
FIG. 5 is a sectional view of the case assembled with an auxiliary device and an auxiliary electrode.
Figure 8:
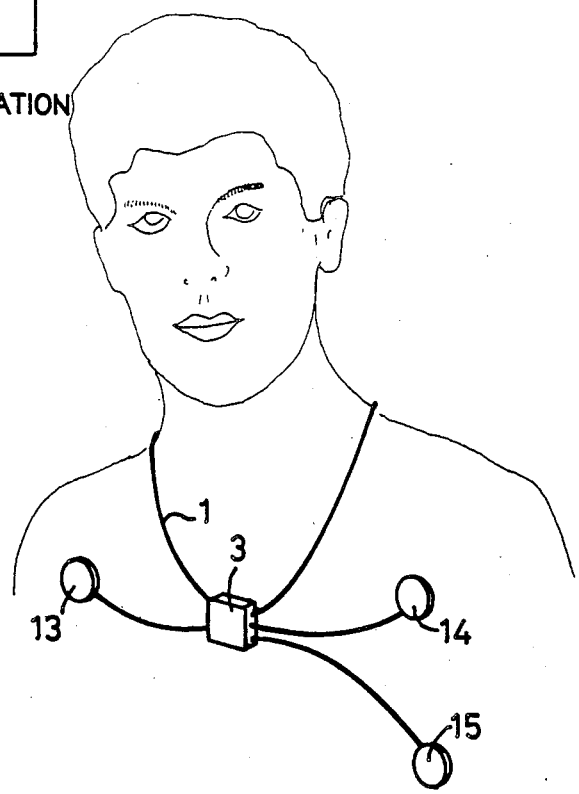
FIG. 8 shows the apparatus with an example of positioning of auxiliary electrodes.

FIG. 5 shows a variant of the apparatus, including an auxiliary device 9 comprising a thin flat case comprising a male coupling 11 on one face and a female coupling 12 on the other face. As shown in FIG. 5, the auxiliary device is disposed between the case 3 and the auxiliary electrode 7. As shown in FIG. 8 the auxiliary device 9 is connected to several other auxiliary electrodes 13, 14 and 15 which adhere to the patient's bust in pre-determined positions.

The auxiliary device 9 comprises an electronic system which is described below.

The apparatus shown in the drawings may be used in various ways. In a first operational mode, it is worn permanently by the patient, the electrode 2 being in permanent contact with the nape of his neck, and when a malaise occurs, the patient presses the case 3 to his chest, which triggers the recording of an electrocardiogram for subsequent interpretation by the specialist doctor. The electronic signal processor includes a memory which can memorize several recordings of a given length, the length and number of the recordings being defined by the doctor. The recordings obtained and memorized can be read directly out of the case 3 by the doctor during consultation of the patients; transmission means can also be provided, for example for transmission over the telephone system, which enable the recordings which have been memorized to be sent to the doctor without a consultation. The triggering of the recording of an electrocardiogram is obtained by means of a control member, such as a push-button 16 is preferably the outer face of the case 3. This push-button 16 is preferably disposed so as not to project from the outer face of the case 3, to avoid untimely triggering of a recording.

In another operational mode of the apparatus illustrated, the case 3 is connected to one or more auxiliary electrodes, such as electrodes 7, 13, 14 and 15, with or without the auxiliary device 9. The apparatus operates in a monitoring or "sentinel" mode, that is to say that it records the electrocardiograms continually in a rotating memory of the electronic processor, and actuation of the push-button 16 causes the fixed memory to register an electrocardiogram corresponding to a period before and after the triggering; this enables an electrocardiogram to be obtained which corresponds to the moment at which the malaise appeared or even a short previous period, and this enables the doctor to establish a more precise diagnosis. This operational mode corresponds to the Holter technique but does not present the disadvantages of this technique, since the apparatus is very light and can be worn very easily. Thus it can be worn for several days without difficulty.

In a third possible operational mode of the apparatus illustrated, the signals recorded are processed to obtain the pulse rate of the user, and advantageously upper and lower thresholds are defined, the processor reacting to a pulse rate exceeding thresholds to give an audible or visual alarm. This function is particularly useful for patients being re-educated, and who have to be careful not to exceed a certain pulse rate. The function is also useful for other users such as sportsmen who may wish to check their pulse rate during training without stopping to feel their pulse. The function is also useful for deep sea divers who also have to check their heart beat, and in this case the alarm is preferably luminous.

FIG. 6 is a block schematic diagram of an embodiment of the electronic processor enclosed in the case 3. The signal produced by electrodes 2 and 5 is first passed to a high input impedance differential amplifier 17, whose output signals are converted to digital signals by an analogue to digital convertor 18. The converter 18 is an 8-bit converter operating at a rate of 100 samples per second, in this example.

The 8-bit signals obtained are passed over a bus 19 to a control and processing logic unit 21, to a digital-to-analogue converter 22 and to memory 23 which is suitably an active memory (RAM) of 16k. A display device 24, of the liquid crystal kind, for example, is controlled by a display control unit 25.

The electronic processor includes a device for transmitting the recordings made; in the example illustrated the transmission device is of the acoustic kind and comprises a voltage controlled oscillator (VCO) 26 which receives the analogue signals supplied by the converter. 25 and whose output signal excites an acoustic transducer 27, comprising a piezo-transducer, for example.

The electronic processor also comprises a circuit 28 which calculates the pulse rate during the recording of the electrocardiogram, for example by a recurrent calculation of the pulse rate from detection of the QRS segment of the electrocardiogram. The apparatus may also comprise a real time clock 29 which is controlled by a quartz 31, for example.

The electronic processor is controlled by a certain number of knobs or push-buttons, among which are the push-button 16 controlling the recording of an electrocardiogram, a knob 32 for controlling the display of the pulse rate, two push-buttons 33 and 34 which set the upper and lower pulse-rate thresholds, a push-button 35 controlling the length of an electrocardiogram recording, a knob 36 controlling the display of the time and a push-button 37 enabling the time of the clock to be set.

The electronic processor apparatus is in the form of an integrated circuit and occupies a very small space. Thus, in one embodiment of the invention, the case 3 has the following dimensions: length 60 mm, width 40 mm, thickness 18 mm and weighs only 100 g.

In the first operational mode described above, actuation of the knob 16 switches the apparatus on and subsequently at the moment of a further actuation of the knob 16 triggers recording of an electrocardiogram whose length has been set by the doctor using the knob 35.

In the second operational mode, the electrode 2 is replaced by the auxiliary electrode 7 or by the set of auxiliary electrodes 7, 13, 14, 15 and 16, through the auxiliary device 9; the electronic records the electrocardiogram continually and, when the knob 16 is actuated, the control unit 21 controls the memorisation of an electrocardiogram corresponding to a period extending before and after the actuation of the knob 16, for example 20 seconds before and 20 seconds after, the length of the recording being set by the push-button 35, once again.

The recordings memorized in digital form in the memory 23 may be read out by the doctor in his surgery or transmitted over the telephone by means of the circuit 26 and the transducer 27 after conversion to analogue form by the converter 22.

In the third operational mode, the apparatus is also in the monitoring state, that is to say the case 3 is connected to the auxiliary electrode 7 and the display shows the pulse rate calculated by the circuit 28. When the pulse rate exceeds one of the values which are preset by means of the push-buttons 33 and 34 and audible or visual alarm is produced.

For this latter operational mode, a simplified version of the apparatus can be made which has no memory nor transmission device. Such apparatus is especially useful for users such as sportsmen.

Figure 7:
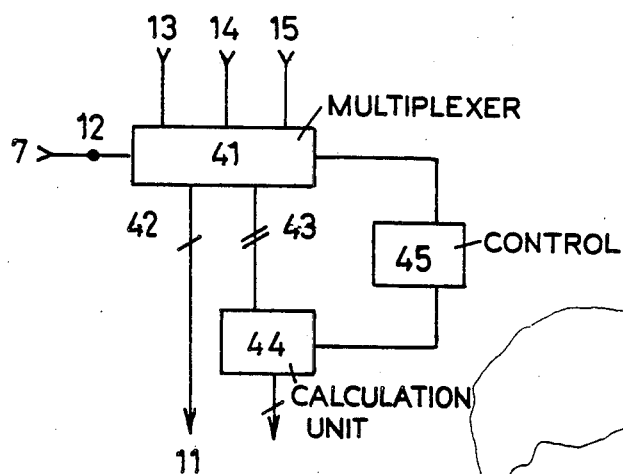
FIG. 7 is a schematic diagram of an example of an electronic circuit in the auxiliary device.

FIG. 7 is a schematic diagram of the circuits in the auxiliary device 9. This device comprises a multiplexer 41 which is connected to the auxiliary electrode 7, which is placed underneath the auxiliary device 9, and to the auxiliary electrodes 13, 14 and 15, which are also preferably ambulatory-type electrodes and which are disposed as shown in FIG. 8 for example, that is to say two electrodes 13, 14 at the top of the patient's chest and an electrode 15 in the region of his heart. The multiplexer output comprises a first line with a single channel 42, which is directly connected to the male coupling and electrical connector member 11, and a second two-channel output 43 which is connected to a signal processing device 44 whose output is also passed to the male connector member 11. The multiplexer 41 and calculation unit 44 are controlled by a control circuit 45.

As a function of the instructions given by the control unit 45, the multiplexer 41 either connects one of the auxiliary electrodes 7, 13, 14 or 15 to one of the inputs of the amplifier 17, so as to obtain a combined signal between the main external electrode 2 and one of the auxiliary electrodes, or it connects two of the auxiliary electrodes to the calculation circuit 44 so as to produce a combined signal which is then passed to the electronic processor of the case 3. In this way, different electrocardiogram graphs can be produced corresponding to the combination of two of the electrodes 2, 7, 13, 14 and 15. The electrocardiogram produced in this way corresponds to those produced by fixed equipment. These recordings are obtained when the apparatus is in the "sentinel" mode, the control circuit 45 causing the different combinations of electrodes to be connected in sequence to the electronic processor of the case 3.

It will be seen that the invention enables electrocardiogram recordings to be obtained very easily in varied circumstances, the handling of the apparatus being very simple. The recording obtained is of high quality and can even be as good as recordings obtained with fixed recording apparatus. The user is very little inconvenienced by wearing the apparatus, and it is always available, whatever clothing the user has put on.

The above description of examples of embodiments of the invention has been given by way of example only, and it is clear that changes and variants can be made within the scope of the invention. In particular, as indicated above, other means can be provided for supporting the electrodes than a harness or shoulder strap. Moreover, the link 1 may be partially spiralled, the part coiled in a spring extending approximately from the collar bone to within a few centimetres of the case.

What is claimed is:

1. A portable apparatus for monitoring heart activity comprising: a case, a first electrode mounted on said case and a second electrode separate from said case wherein said first and second electrodes are for making electrical contact with respective regions of the patient's body to pick up electrical heart signals; attachment means for attaching said apparatus to a patient's body including flexible loop for passing round a part of the patient's body; wherein said case includes electronic processing means for registering said electrical heart signals; electrical connection means connecting said first electrode to said electronic processing means; said loop including electrical conductor means for connecting said second electrode electrically with said electronic processing means; and at least one auxiliary electrode electrically connected to the electronic processing means, fixing means for fixing said auxiliary electrode to the patient's skin, and connection means for connecting said auxiliary electrode with said case wherein said connection means for connecting said auxiliary electrode includes mechanical and electrical couplings for coupling said first electrode to said auxiliary electrode.

2. Apparatus as claimed in claim 1, wherein said connection means for connecting said auxiliary electrode includes an auxiliary case of generally thin and flat shape presenting two faces on which are disposed male and female coupling members respectively, whereby said auxiliary case may be connected electrically and mechanically with said electrical connection means between said case and said auxiliary electrode, further auxiliary electrodes, fixing means for fixing said further auxiliary electrodes to different regions of the patient's bust, and flexible electrical connector means for connecting said further auxiliary electrodes with said auxiliary case.

3. Apparatus as claimed in claim 2, wherein said electronic processing means includes analogue-to-digital converter means responsive to signals from said electrodes, digital storage means for storing signals from said analogue-to-digital converter means, and manually actuable trigger means for triggering storage of said signals in said storage means.

4. Apparatus as claimed in claim 2, wherein said fixing means comprises adhesive material applied to faces of said auxiliary electrodes.

5. Apparatus as claimed in claim 2, wherein said auxiliary case includes multiplexer means for passing signals from selected auxiliary electrodes to said electronic processing means.

6. Apparatus as claimed in claim 1 wherein said first and second electrodes are flexible and comprise interwoven conductors.

7. Apparatus as claimed in claim 1, wherein said electronic processing means includes analogue-to-digital converter means responsive to signals from said electrodes, digital storage means for storing signals from said analogus-to-digital converter means, and manually actuable trigger means for triggering storage of said signals in said storage means.

8. Apparatus as claimed in claim 1, including means establishing pre-set threshold pulse rate values and alarm means operatively connected thereto, wherein said electronic processing means includes means responsive to the patient's pulse rate relative to said pre-set threshold values for providing an alarm when the pulse rate exceeds said threshold values.

9. Apparatus as claimed in claim 1, wherein said fixing means comprises adhesive material applied to faces of said auxiliary electrodes.

10. Apparatus as claimed in claim 1, wherein said electronic processing means includes transmission means for generating an acoustic signal stated to said electrocardiogram signals for transmission to a remote receiver.

11. Apparatus as claimed in claim 1, wherein said first and second electrodes are flexible and comprise interwoven conductors.

12. Apparatus as claimed in claim 1, wherein said first and second electrodes are flexible and comprise interwoven conductors.

13. Apparatus as claimed in claim 1, wherein said electronic processing means includes analogus-to-digital converter means responsive to signals from said electrodes, digital storage means for storing signals from said analog-to-digital converter means, and manually actuable trigger means for triggering storage of said signals in said storage means.

* * * * *